United States Patent [19]

Bundy

[11] 4,130,584

[45] Dec. 19, 1978

[54] 9-DEOXY-9-METHYLENE-PGF SULFONYLAMIDES

[75] Inventor: Gordon L. Bundy, Portage, Mich.

[73] Assignee: The Upjohn Company, Kalamazoo, Mich.

[21] Appl. No.: 894,271

[22] Filed: Apr. 7, 1978

Related U.S. Application Data

[63] Continuation-in-part of Ser. No. 786,250, Apr. 11, 1977, Pat. No. 4,098,805.

[51] Int. Cl.² .......................................... C07C 177/00
[52] U.S. Cl. ........................ 260/556 A; 260/556 AR
[58] Field of Search ..................... 260/556 A, 556 AR

[56] References Cited

PUBLICATIONS

Derwent Abstract, 05786U-BC NL 7209738-Q, 16-0-1-73.
Derwent Abstract, 76383T-B NL 7206361-Q, 14-1-1-72.
Derwent Abstract, 219084/13 BE 846-650, 28-03-77.

Primary Examiner—Paul J. Killos
Attorney, Agent, or Firm—Robert A. Armitage

[57] ABSTRACT

The present invention relates to novel 9-deoxy-9-methylene-PGF-sulfonylamides. These compounds are useful pharmacological agents, and are useful for the same purposes as the corresponding 9-deoxy-9-methylene-PGF-type acids.

32 Claims, No Drawings

9-DEOXY-9-METHYLENE-PGF SULFONYLAMIDES

CROSS REFERENCE TO RELATED APPLICATIONS

This application is a continuation-in-part of Ser. No. 786,250, filed Apr. 11, 1977, now U.S. Pat. No. 4,098,805, issued July 4, 1978.

The present invention relates to novel 9-deoxy-9-methylene-PGF-sulfonylamides, the essential material constituting a disclosure of which is incorporated here by reference from U.S. Pat. No. 4,098,805.

I claim:

1. A prostaglandin analog of the formula

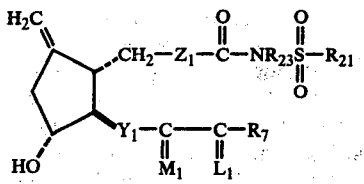

wherein $Y_1$ is trans—CH=CH—, —C≡C—, or —$CH_2CH_2$— wherein $M_1$ is

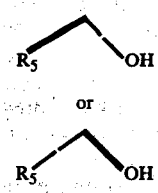

or

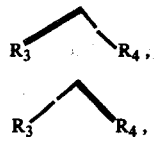

wherein $R_5$ is hydrogen or methyl;
wherein $L_1$ is

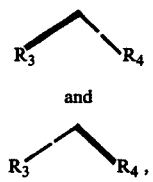

or a mixture of wherein $R_3$ and $R_4$ are hydrogen, methyl, or fluoro, being the same or different, with the proviso that one of $R_3$ and $R_4$ is fluoro only when the other is hydrogen or fluoro;

wherein $Z_1$ is
(1) cis—CH=CH—$CH_2$—$(CH_2)_g$—$CH_2$—,
(2) cis—CH=CH—$CH_2$—$(CH_2)_g$—$CF_2$,
(3) cis—$CH_2$—CH=CH—$(CH_2)_g$—$CH_2$—,
(4) —$(CH_2)_3$—$(CH_2)_g$—$CH_2$—,
(5) —$(CH_2)_3$—$(CH_2)_g$—$CF_2$—,
(6) —$CH_2$—O—$CH_2$—$(CH_2)_g$—$CH_2$—,
(7) —C≡C—$CH_2$—$(CH_2)_g$—$CH_2$—,
(8) —$CH_2$—C≡C—$(CH_2)_g$—$CH_2$—, (9) 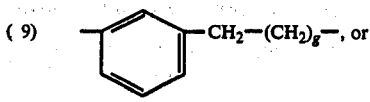

(10) 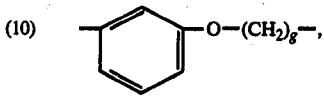

wherein g is one, 2 or 3;
wherein $R_7$ is
(1) —$(CH_2)_m$—$CH_3$, (2) 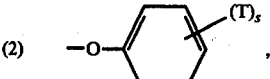, or (3) 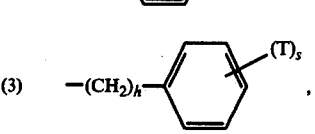, wherein m is one to 5, inclusive, h is zero or one, T is chloro, fluoro, trifluoromethyl, alkyl of one to 3 carbon atoms, inclusive, or alkoxy of one to 3 carbon atoms, inclusive, and s is zero, one, 2 or 3, the various T's being the same or different, with the proviso that not more then two T's are other than alkyl, with the further proviso that $R_7$ is

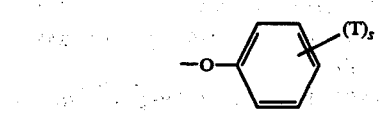

wherein T and s are as defined above, only when $R_3$ and $R_4$ are hydrogen or methyl, being the same or different; and wherein $R_{21}$ is hydrogen, alkyl of one to 12 carbon inclusive; aralkyl of 7 to 12 carbon atoms, inclusive, phenyl, phenyl substituted with one, 2, or 3 chloro or alkyl of one to 3 carbon atoms, inclusive, or phenyl substituted with hydroxycarbonyl or alkoxycarbonyl of one to 4 carbon atoms, inclusive; and $R_{23}$ is hydrogen or alkyl of one to 4 carbon atoms.

2. A prostaglanin analog according to claim 1, wherein $Y_1$ is —C≡C—.

3. 9-Deoxy-9-methylene-13,14-didehydro-$PGR_2$, methylsulfonylamide, a prostaglandin analog according to claim 2.

4. A prostaglandin analog according to claim 1, wherein $Y_1$ is —$CH_2CH_2$—.

5. 9-Deoxy-9-methylene13,14-dihydro-$PGF_2$, methylsulfonylamide, a prostaglandin analog according to claim 4.

6. A prostaglandin analog according to claim 1, wherein $Y_1$ is trans—CH=CH—.

7. A prostaglandin analog according to claim 6, wherein $Z_1$ is aromatic.

8. 9-Deoxy-9-methylene-3,7-inter-m-phenylene-3-oxa-4,5,6-trinor-$PGF_1$, methylsulfonylamide, a prostaglandin analog according to claim 7.

9. 9-Deoxy-9-methylene-3,7-inter-m-phenylene-4,5,6-trinorPGF$_1$, methylsulfonylamide, a prostaglandin analog according to claim 7.

10. A prostaglandin analog according to claim 6, wherein Z$_1$ is aliphatic.

11. A prostaglandin analog according to claim 10, wherein M$_1$ is

12. 15-epi-9-Deoxy-9-methylene-PGF$_2$, methylsulfonylamide, a prostaglandin analog according to claim 11.

13. A prostaglandin analog according to claim 10, wherein M$_1$ is

14. A prostaglandin analog according to claim 13, wherein Z$_1$ is cis—CH=CH—CH$_2$—(CH$_2$)$_g$—CH$_2$—.

15. A prostaglandin analog according to claim 14, wherein R$_7$ is

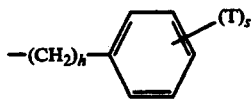

16. 9-Deoxy-9-methylene-17-phenyl-18,19,20-trinor-PGF$_2$, methylsulfonylamide, a prostaglandin analog according to claim 15.

17. A prostaglandin analog according to claim 14, wherein R$_7$ is

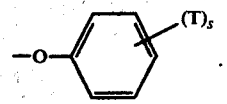

18. 9-Deoxy-9-methylene-16-phenoxy-17,18,19,20-tetranor-PGF$_2$, methylsulfonylamide, a prostaglandin analog according to claim 17.

19. A prostaglandin analog according to claim 14, wherein R$_7$ is —(CH$_2$)$_m$—CH$_3$.

20. A prostaglandin analog according to claim 19, wherein m is 3.

21. A prostaglandin analog according to claim 20, wherein g is 3.

22. 2a, 2b-Dihomo-9-deoxy-9-methylene-15-methyl-PGF$_2$, methylsulfonylamide, a prostaglandin analog according to claim 21.

23. A prostaglandin analog according to claim 20, wherein g is one.

24. A prostaglandin analog according to claim 23, wherein at least one of R$_3$ and R$_4$ is methyl.

25. 9-Deoxy-9-methylene-16,16-dimethyl-PGF$_2$, methylsulfonylamide, a prostaglandin analog according to claim 24.

26. A prostaglandin analog according to claim 23, wherein at least one of R$_3$ and R$_4$ is fluoro.

27. 9-Deoxy-9-methylene-16,16-difluoro-PGF$_2$, methylsulfonylamide, a prostaglandin analog according to claim 26.

28. A prostaglandin analog according to claim 23, wherein R$_3$ and R$_4$ are both hydrogen.

29. A prostaglandin analog according to claim 28, wherein R$_5$ is methyl.

30. 9-Deoxy-9-methylene-15-methyl-PGF$_2$, methylsulfonylamide, a prostaglandin analog according to claim 29.

31. A prostaglandin analog according to claim 28, wherein R$_5$ is hydrogen.

32. 9-Deoxy-9-methylene-PGF$_2$, methylsulfonylamide, a prostaglandin analog according to claim 31.

* * * * *

UNITED STATES PATENT OFFICE
CERTIFICATE OF CORRECTION

Patent No. 4,130,584  Dated  December 19, 1978

Inventor(s) Gordon L. Bundy

It is certified that error appears in the above-identified patent and that said Letters Patent are hereby corrected as shown below:

Column 1, line 62, "(2) cis-$CH=CH-CH_2-(CH_2)_g-CF_2$," should read -- (2) cis-$CH=CH-CH_2-(CH_2)_g-CF_2-$, --;

Column 2, line 54, "$PGR_2$" should read -- $PGF_2$ --.

Signed and Sealed this

Third Day of April 1979

[SEAL]

Attest:

RUTH C. MASON
Attesting Officer

DONALD W. BANNER
Commissioner of Patents and Trademarks